(12) United States Patent
Auld et al.

(10) Patent No.: US 8,808,318 B2
(45) Date of Patent: Aug. 19, 2014

(54) SURGICAL PROBE WITH INCREASED FLUID FLOW

(75) Inventors: Jack Robert Auld, Laguna Niguel, CA (US); Brian William McDonell, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 166 days.

(21) Appl. No.: 13/036,401

(22) Filed: Feb. 28, 2011

(65) Prior Publication Data
US 2012/0221033 A1    Aug. 30, 2012

(51) Int. Cl.
*A61F 9/00* (2006.01)

(52) U.S. Cl.
USPC ............................ 606/166; 606/171; 604/22

(58) Field of Classification Search
CPC ... A61F 9/013; A61F 9/0133; A61F 9/00736; A61F 9/00745; A61F 9/00754; A61F 9/00763; A61B 17/32002
USPC ................... 606/169, 170, 171, 180; 604/22; 600/566, 567
See application file for complete search history.

(56) References Cited

U.S. PATENT DOCUMENTS

| | | |
|---|---|---|
| 812,162 A | 2/1906 | Bemis |
| 2,016,746 A | 10/1935 | Ireland |
| 2,707,389 A | 5/1955 | Fortier |
| 3,084,674 A | 4/1963 | Watson |
| 3,477,665 A | 11/1969 | Legrand |
| 3,646,727 A | 3/1972 | Wachsmuth |
| 3,703,139 A | 11/1972 | Furlong |
| 3,854,382 A | 12/1974 | Walters et al. |
| 3,867,934 A | 2/1975 | Ollivier |
| 4,077,567 A | 3/1978 | Ginn et al. |
| 4,086,804 A | 5/1978 | Ruby |
| 4,164,167 A | 8/1979 | Imai et al. |
| 4,168,707 A | 9/1979 | Douvas et al. |
| 4,246,902 A * | 1/1981 | Martinez .................. 604/22 |

(Continued)

FOREIGN PATENT DOCUMENTS

| | | |
|---|---|---|
| DE | 3925405 A1 | 2/1991 |
| DE | 4232586 A1 | 3/1994 |

(Continued)

OTHER PUBLICATIONS

Buchanan, P.R., et al.,"Recovery of ventilation distributions by gas wash-out of a mechanical pump", Clinical Physics and Physiological Measurement, 1986, 7(3).

(Continued)

*Primary Examiner* — Kathleen Holwerda

(57) ABSTRACT

A surgical probe, e.g. a vitrectomy probe, and methods of making the same are disclosed. An exemplary surgical probe may include a tubular body and a cutting tool that is received within the body. The tubular body may define a cutting aperture that is adjacent a first end of the body and a fluid passage that extends through the body from the cutting aperture to a second end of the body. The cutting tool may be received within the body and disposed within the fluid passage. The cutting tool is generally configured to allow fluid flow through the cutting tool. The cutting tool may include a body portion and a blade portion that is configured to cut material entering the cutting aperture. The body portion may extend only partially about an inner circumference of the tubular body.

8 Claims, 2 Drawing Sheets

(56) References Cited

U.S. PATENT DOCUMENTS

| | | |
|---|---|---|
| 4,253,480 A | 3/1981 | Kessel et al. |
| 4,323,064 A | 4/1982 | Hoenig et al. |
| 4,331,130 A | 5/1982 | Lewicky |
| 4,344,144 A | 8/1982 | Damico et al. |
| 4,476,532 A | 10/1984 | Akiyama et al. |
| 4,590,935 A | 5/1986 | Ranalli |
| 4,622,503 A | 11/1986 | Sundblom et al. |
| 4,650,460 A | 3/1987 | Roizenblatt |
| 4,650,462 A | 3/1987 | DeSatnick et al. |
| 4,678,459 A | 7/1987 | Onik et al. |
| 4,679,583 A | 7/1987 | Lucas et al. |
| 4,696,298 A | 9/1987 | Higgins et al. |
| 4,706,687 A | 11/1987 | Rogers et al. |
| 4,757,814 A | 7/1988 | Wang et al. |
| 4,770,654 A | 9/1988 | Rogers et al. |
| 4,790,816 A | 12/1988 | Sundblom et al. |
| 4,810,242 A | 3/1989 | Sundblom et al. |
| 4,840,111 A | 6/1989 | Garnjost |
| 4,933,843 A | 6/1990 | Scheller et al. |
| 4,985,027 A | 1/1991 | Dressel |
| 5,019,035 A | 5/1991 | Missirlian et al. |
| 5,020,315 A | 6/1991 | Leachman, Jr. et al. |
| 5,020,825 A | 6/1991 | Lizell |
| 5,024,654 A | 6/1991 | Tyler |
| 5,092,178 A | 3/1992 | Vanderlaan |
| 5,094,260 A | 3/1992 | Stuart et al. |
| 5,154,207 A | 10/1992 | Bolt |
| 5,176,628 A | 1/1993 | Charles et al. |
| 5,217,465 A | 6/1993 | Steppe |
| 5,239,861 A | 8/1993 | Fujita et al. |
| 5,314,295 A | 5/1994 | Lukkari et al. |
| 5,322,505 A * | 6/1994 | Krause et al. .............. 604/24 |
| 5,380,280 A | 1/1995 | Peterson |
| 5,403,276 A | 4/1995 | Schechter et al. |
| 5,417,246 A | 5/1995 | Perkins et al. |
| 5,549,139 A | 8/1996 | Perkins et al. |
| 5,571,248 A | 11/1996 | Seetharaman et al. |
| 5,580,347 A | 12/1996 | Reimels |
| 5,587,536 A | 12/1996 | Rasmussen |
| 5,674,194 A | 10/1997 | Jung et al. |
| 5,690,660 A * | 11/1997 | Kauker et al. ............. 606/180 |
| 5,829,335 A | 11/1998 | Ewald et al. |
| 5,846,257 A | 12/1998 | Hood |
| 5,857,485 A | 1/1999 | Perkins et al. |
| 5,911,701 A * | 6/1999 | Miller et al. .............. 604/22 |
| 5,979,494 A | 11/1999 | Perkins et al. |
| 5,989,262 A | 11/1999 | Josephberg |
| 6,155,233 A | 12/2000 | Wade et al. |
| 6,162,187 A | 12/2000 | Buzzard et al. |
| 6,450,966 B1 | 9/2002 | Hanna |
| 6,485,436 B1 | 11/2002 | Truckai et al. |
| 6,514,268 B2 | 2/2003 | Finlay et al. |
| 6,527,736 B1 | 3/2003 | Attinger et al. |
| 6,568,416 B2 | 5/2003 | Tucker et al. |
| 6,575,990 B1 | 6/2003 | Wang et al. |
| 6,610,059 B1 * | 8/2003 | West, Jr. .............. 606/41 |
| 6,678,584 B2 | 1/2004 | Junk et al. |
| 6,736,980 B2 | 5/2004 | Moscaritolo |
| 6,779,541 B2 | 8/2004 | Inayama et al. |
| 7,219,691 B2 | 5/2007 | Gethmann et al. |
| 7,244,240 B2 | 7/2007 | Nazarifar et al. |
| 7,335,217 B2 | 2/2008 | Wang et al. |
| 7,337,041 B2 | 2/2008 | Junk et al. |
| 7,470,277 B2 | 12/2008 | Finlay et al. |
| 7,628,054 B2 | 12/2009 | Hajishah et al. |
| 7,775,052 B2 | 8/2010 | Cornwell et al. |
| 8,038,692 B2 | 10/2011 | Valencia et al. |
| 8,080,029 B2 | 12/2011 | Charles |
| 8,105,405 B2 | 1/2012 | Turner et al. |
| 8,157,145 B2 | 4/2012 | Shelton, IV et al. |
| 8,162,000 B2 | 4/2012 | Turner et al. |
| 2006/0129062 A1 | 6/2006 | Nicoson et al. |
| 2006/0271082 A1 | 11/2006 | Kirchhevel et al. |
| 2007/0270735 A1 | 11/2007 | Williams et al. |
| 2007/0270746 A1 | 11/2007 | King |
| 2007/0282262 A1 | 12/2007 | Williams et al. |
| 2008/0082077 A1 | 4/2008 | Williams |
| 2008/0103433 A1 | 5/2008 | Nazarifar et al. |
| 2008/0146988 A1 | 6/2008 | Olivera et al. |
| 2008/0149197 A1 | 6/2008 | Turner et al. |
| 2008/0168985 A1 | 7/2008 | Turner et al. |
| 2008/0172078 A1 | 7/2008 | Svetic |
| 2009/0124962 A1 | 5/2009 | Hopkins et al. |
| 2009/0203480 A1 | 8/2009 | Petzold et al. |
| 2009/0259242 A1 | 10/2009 | Gerg et al. |
| 2009/0287233 A1 | 11/2009 | Huculak |
| 2010/0145374 A1 | 6/2010 | Perkins et al. |
| 2010/0312169 A1 | 12/2010 | Auld et al. |
| 2011/0054508 A1 | 3/2011 | Zhou et al. |
| 2011/0144675 A1 | 6/2011 | Gao et al. |
| 2011/0295293 A1 | 12/2011 | Agahi |
| 2012/0157906 A1 | 6/2012 | Underwood et al. |
| 2012/0157908 A1 | 6/2012 | Underwood et al. |
| 2012/0157909 A1 | 6/2012 | Underwood et al. |
| 2012/0158006 A1 | 6/2012 | McDonell |
| 2012/0158029 A1 | 6/2012 | Underwood et al. |
| 2012/0158030 A1 | 6/2012 | Underwood et al. |
| 2013/0053759 A1 | 2/2013 | McCawley |

FOREIGN PATENT DOCUMENTS

| | | |
|---|---|---|
| DE | 19821420 C1 | 10/1999 |
| DE | 10247869 A1 | 5/2004 |
| DE | 202005009670 U1 | 9/2005 |
| EP | 0626628 B1 | 11/1994 |
| EP | 0673475 B1 | 9/1995 |
| EP | 0469641 B1 | 12/1995 |
| EP | 0874163 A2 | 10/1998 |
| EP | 0884667 A1 | 12/1998 |
| EP | 1172586 B1 | 3/2004 |
| EP | 1074271 B1 | 10/2004 |
| GB | 792397 | 3/1958 |
| GB | 1213723 | 11/1970 |
| GB | 1323788 | 7/1973 |
| GB | 2016746 A | 9/1979 |
| GB | 2140871 A | 12/1984 |
| GB | 2389423 A | 12/2003 |
| JP | 7259801 A | 10/1995 |
| JP | 9225698 A | 9/1997 |
| JP | 9311091 A | 12/1997 |
| WO | 95/31141 A1 | 11/1995 |
| WO | 00/78371 A1 | 12/2000 |
| WO | 01/30281 A1 | 5/2001 |
| WO | 01/64120 A1 | 9/2001 |
| WO | 2005/028126 A1 | 3/2005 |
| WO | 2008/000599 A1 | 1/2008 |
| WO | 2008/054944 A1 | 5/2008 |
| WO | 2008079526 A2 | 7/2008 |
| WO | 2008/105950 A2 | 9/2008 |
| WO | 2008140537 A1 | 11/2008 |
| WO | 2008147429 A2 | 12/2008 |
| WO | 2010/066302 A1 | 6/2010 |
| WO | 2011/025658 A1 | 3/2011 |
| WO | 2011/071655 A1 | 6/2011 |
| WO | 2011/149621 A1 | 12/2011 |

OTHER PUBLICATIONS

Ellis, G., et al., "Microcomputer-Controlled Precision Pressure Generator", IEEE Transactions on Instrumentation and Measurement, 1977, 214-217, 26(3).

Johnson, K.S., et al, "A submersible flow analysis system", Analytical Chimica Acta, 1986, 245-257, 179.

Kabei, S., et al, "A portable pneumatic driving unit for a left ventricular assist device", Int. J. Artif. Organs, 1988, 186-90, 11(3).

Nachlas, M., et al., "A simple portable pneumatic pump for external cardiac massage", The American Journal of Cardiology, 1962, 107-09, 10(1).

Rogers, R.C., "An inexpensive picoliter-volume pressure ejection system", Brain Research Bulletin, 1985, 669-71, 15(6).

(56) References Cited

OTHER PUBLICATIONS

Tabassum, A.A., "Solar refrigeration: evaluation of technical options and design of a solar-generator-absorber for a novel adsorption refrigerator", Tabassum thesis, Cranfield University, 1989.

Turkentine, R.B., et al., "Pressure-operated shutter for thin-film monitor", Journal of Physics E: Scientific Instruments, 1979, 12(1).

Waldeck, J.L., "The development of a portable pressure source for the static and dynamic calibration of pressure transducers", The Journal of Wind Engineering and Industrial Aerodynamics, 1987, 213-30, 26(2).

Whalen, R.L., et al., "An electromagnetic pneumatic blood pump driver", American Society of Artificial Internal Organs, 1988, 721-25, 34(3).

McDonell, B.W., Optimized Pneumatic Drive Lines, U.S. Appl. No. 13/314,625, filed Dec. 8, 2011, 32 pgs.

* cited by examiner

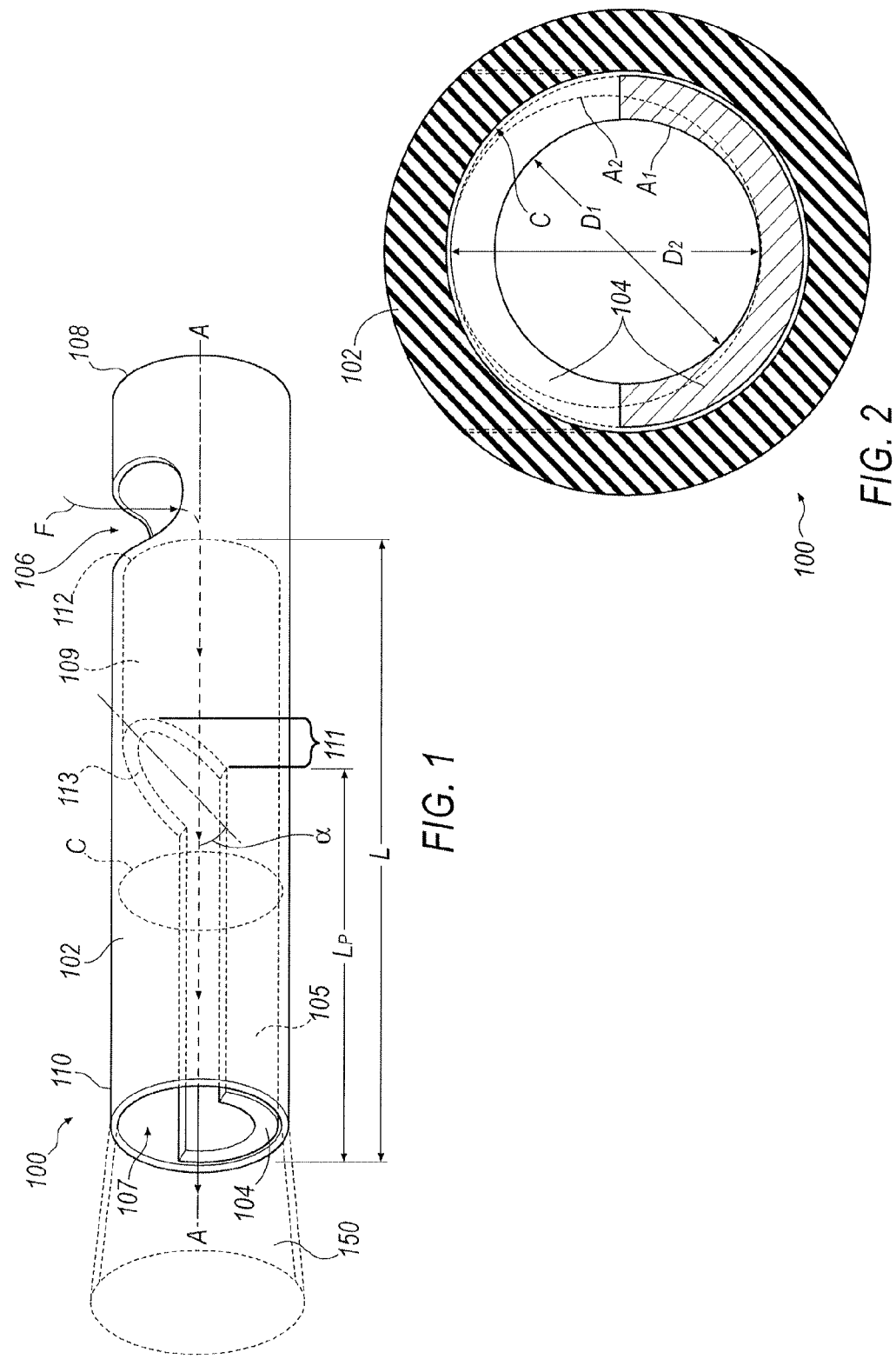

SURGICAL PROBE WITH INCREASED FLUID FLOW

BACKGROUND

Many microsurgical procedures require precision cutting and/or removal of various body tissues. For example, vitreoretinal surgery often requires the cutting, removal, dissection, delamination, coagulation, or other manipulation of delicate tissues such as the vitreous humor, traction bands, membranes, or the retina. The vitreous humor, or vitreous, is composed of numerous microscopic fibers that are often attached to the retina. Therefore, cutting, removal, or other manipulation of the vitreous must be done with great care to avoid traction on the retina, the separation of the retina from the choroid, a retinal tear, or, in the worst case, cutting and removal of the retina itself.

Microsurgical instruments, such as vitrectomy probes, fiber optic illuminators, infusion cannulas, aspiration probes, scissors, forceps, and lasers are typically utilized during vitreoretinal surgery. These devices are generally inserted through one or more surgical incisions in the sclera near the pars plana, which are called sclerotomies. Generally, a cutting blade disposed within a tubular probe needle moves reciprocally within the probe needle, thereby cutting material, e.g., vitreous humor, with a blade edge that translates relative to an aperture in the needle. At the same time, the humor is drawn away from the cutting site through the aperture. For example, suction may be applied to draw the humor away from the aperture, continuing through the needle.

To minimize the size of the surgical incisions necessary to perform these procedures, probe needles are designed in progressively smaller sizes. As probe size decreases, maximizing fluid flow through the needle becomes increasingly important. The cutting blade, which must be strong enough to resist buckling from the high speed reciprocal motion within the needle, necessarily reduces flow as it obstructs a portion of the needle. Accordingly, there is a need for an improved probe needle that reduces overall size while providing adequate flow through the needle.

BRIEF DESCRIPTION OF THE DRAWINGS

While the claims are not limited to the illustrated examples, an appreciation of various aspects is best gained through a discussion of various examples thereof. Referring now to the drawings, illustrative examples are shown in detail. Although the drawings represent the various examples, the drawings are not necessarily to scale and certain features may be exaggerated to better illustrate and explain an innovative aspect of an example. Further, the examples described herein are not intended to be exhaustive or otherwise limiting or restricting to the precise form and configuration shown in the drawings and disclosed in the following detailed description. Exemplary illustrations of the present invention are described in detail by referring to the drawings as follows.

FIG. 1 illustrates a perspective view of an exemplary surgical probe;

FIG. 2 illustrates a cross sectional view of an exemplary surgical probe;

DETAILED DESCRIPTION

Figure 3:
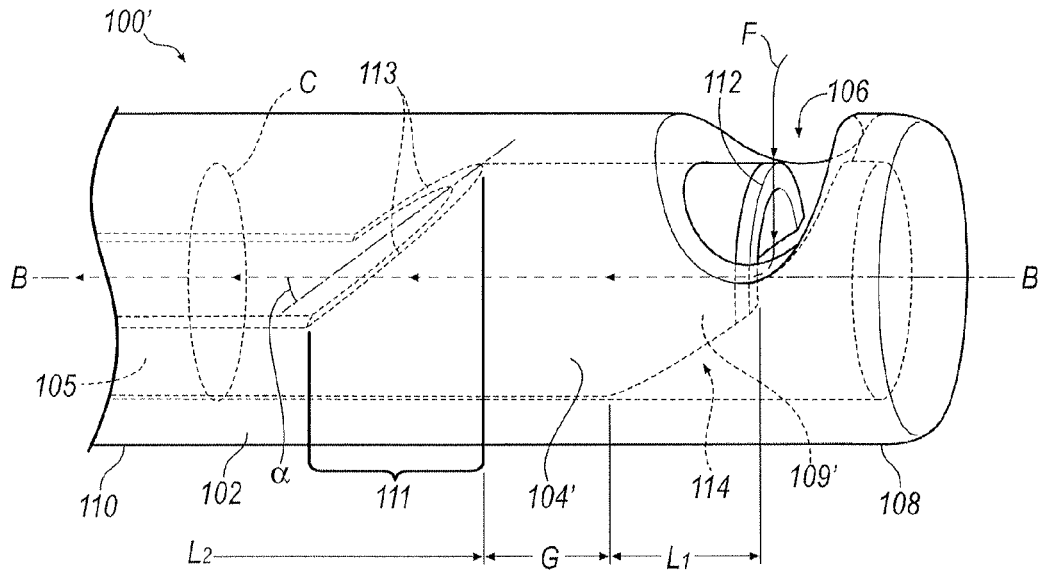
FIG. 3 illustrates a perspective view of another exemplary surgical probe.

Various exemplary illustrations of a surgical probe, e.g. a vitrectomy probe, are disclosed herein. An exemplary surgical probe may include a tubular body and a cutting tool that is received within the body. The tubular body may define a cutting aperture that is adjacent a first end of the body and a fluid passage that extends through the body from the cutting aperture to a second end of the body. The cutting tool may be received within the body and disposed within the fluid passage. The cutting tool is generally configured to allow fluid flow through the cutting tool. The cutting tool may define a body portion and a blade portion disposed at a first end of the body portion. The blade portion may be configured to cut material entering the cutting aperture. The body portion of the cutting tool may extend only partially about an inner circumference of the tubular body.

An exemplary method of forming a surgical probe, such as a vitrectomy probe, may include providing a tubular body defining a cutting aperture adjacent a first end of the body. The tubular body may define a fluid passage extending through the body from the cutting aperture to a second end of the body. The method may further include forming a cutting tool having a body portion and a blade portion, including removing a portion of a tubular blank from the body portion such that the body portion extends only partially about an inner circumference of the tubular body. The method may further include inserting the cutting tool into the fluid passage of the tubular body such that the blade portion is positioned adjacent the cutting aperture. The cutting tool may be configured to allow fluid flow through the cutting tool.

Generally, flow performance of a surgical probe is influenced by a pressure drop through the probe. If the pressure drop across any segment of a surgical probe can be reduced, overall flow of the probe may be increased. Accordingly, by reducing constriction of the fluid passage by the cutter tube, an increase in flow may be realized. Pressure drop may generally be proportional to a length of the cutter tube. At the same time, for round cross sections, pressure drop will decrease with an increase in diameter or cross sectional area of the cutter tube. More specifically, this is explained by Poiseuille's equation, below:

$$\Delta P = \frac{128 \, \mu L Q}{\pi D^4};$$

where:
$\mu$=dynamic viscosity
L=Length of tube
Q=volumetric flow rate
D=inside diameter For a given pressure drop, $\Delta P$, the flow, Q, is therefore proportional to the inside diameter of the cutter tube, D, to the fourth power:

$$Q \propto D^4 \Delta P$$

Accordingly, pressure drop may be reduced substantially by enlarging the inside diameter of the cutter tube. At the same time, any reductions in the surface, or material of the cutter tube, may need to be balanced against the need for stability in the cutter tube, e.g., to prevent buckling of the tube during cutting.

As seen above in Poiseuille's equation, cross sectional area alone may not determine flow resistance. Rather, the overall cross sectional geometry, including the diameter to the fourth power as one component, determines the flow resistance. Therefore, an increase in cross sectional area alone may not be sufficient to ensure increased flow in all cases. The cross sectional geometries being compared herein for flow resistance are substantially circular or nearly so and, most importantly, the geometry of the examples having smaller cross-sectional areas can be usually be completely contained within the geometry of examples having larger cross-sectional areas. Accordingly, a greater cross-sectional area in these cases will result in reduced flow resistance.

Referring now to FIGS. 1 and 2, an exemplary surgical probe 100 is illustrated. Surgical probe 100 may be any type of surgical probe, for example, a vitrectomy probe. The surgical probe 100 may include a tubular body 102 that defines a cutting aperture 106 adjacent a first end 108 of the body 102. The surgical probe 100 may further include a cutting tool 104 that is received within the body 102. The cutting tool 104 may have a body portion 105 and a blade portion 109. Where probe 100 is a vitrectomy probe, the cutting tool 104 may be configured to translate axially within the tubular body 102, thereby cutting or slicing material such as vitreous humor entering the cutting aperture 106, as will be described further below.

The probe 100 may have the first end 108 configured to be inserted into a surgical incision, e.g., during a vitrectomy procedure. A second end 110 may be secured to a surgical tool (not shown) for fluid exchange therewith, to allow suction or removal of material entering the cutting aperture 106. Accordingly, the second end 110 may generally define a fluid aperture 107 in fluid communication with the cutting aperture 106.

The tubular body 102 generally defines a passage for a fluid flow F extending through the body from the cutting aperture 106 to the aperture 107 in the second end 110 of the body 102. The cutting tool 104 is generally disposed within the passage, and is configured to allow fluid flow F to flow through the cutting tool 104. For example, the cutting tool 104 may be generally tubular, e.g., along the blade portion 109, defining a central aperture through the cutting tool 104. The blade portion 109 may define a blade 112 that is configured to cut material that extends or is drawn into tubular body 102 through cutting aperture 106, e.g., vitreous humor during a vitrectomy procedure. For example, the cutting tool 104 may be reciprocated within the tubular body 102 such that the blade 112 moves across the cutting aperture 106, thereby cutting material that enters the aperture 106. The blade 112 may extend at least partially about an end of the cutting tool 104 that is adjacent the cutting aperture 106.

In one exemplary illustration, the blade portion 109 of the cutting tool 104 may define a shape generally corresponding to inner surface of the tubular body 102 along the portion $L_P$ of the cutting tool 104. For example, as shown in FIGS. 1 and 2, both the blade portion 109 and the tubular body 102 define a generally cylindrical shape. Further, the cutting tool 104 may be sized such that it may be received within the tubular body to allow reciprocal motion of the cutting tool 104 to facilitate the cutting action of the cutting tool 104. The cutting tool 104, e.g., along the blade portion 109, may define a generally fluid-tight fit against inner surfaces of the tubular body 102, thereby substantially forcing a fluid flow F through the tubular body 102 to pass through the cutting tool 104, as generally shown in FIGS. 1 and 3.

In another exemplary illustration, the body portion 105 of the cutting tool 104 may generally extend only partially about an inner circumference C of the tubular body 102. More specifically, the body portion 105 may generally extend along a portion $L_P$ of an entire length L of the cutting tool 104. As best seen in FIG. 1, the body portion 105 cutting tool 104 generally has an upper half of the tubular shape removed along the length $L_P$ of the cutting tool 104. By removing at least a portion of the otherwise generally cylindrical cutting tool 104, fluid flow is advantageously increased through the surgical probe 100. More specifically, the geometry is generally opened up to increase fluid flow F through the body portion 105 of the cutting tool 104, thereby effectively reducing a pressure drop across the cutting tool 104 within the probe 100. Any portion of the cutting tool 104 may be removed, e.g., by cutting or grinding away portions of a tubular stock used to form the cutting tool 104. In another exemplary illustration, electrical discharge machining (EDM) may be employed to remove material from the cutting tool 104. In the examples shown in FIGS. 1 and 2, the body portion 105 of the cutting tool 104 extends about no more than approximately one half of the inner circumference C of the tubular body 102.

The cross-sectional area normal to the fluid flow F along the body portion 105 of the cutting tool is shown in FIG. 2. The cross sectional area of the fluid flow F along the body portion 105 illustrated in FIG. 2 may generally include two substantially semispherical components defined along the lower half by the cutting tool 104, and along the upper half by the tubular body 102.

The enlarged cross-sectional area presented by the cutting tool 104 and tubular body 102 along the body portion 105 of the cutting tool 104 has an effective diameter $D_2$ that is greater than the diameter $D_1$ of the cutting tool 104. Accordingly, the fluid flow cross sectional area $A_2$ that is presented by the surgical probe 100, represented schematically in FIG. 2, is larger than the cross-sectional area $A_1$ presented by the inside diameter $D_1$ of the cutting tool 104. A maximum width or diameter $D_2$ of the probe 100 is therefore larger than an inner diameter $D_1$ defined by the cutting tool 104.

The opening up of the geometry of the cutting tool 104 by removing the upper half of the generally tubular shape, including the enlarged cross-sectional area $A_2$ along the body portion 105 of the cutting tool 104, results in reduced flow resistance, and therefore in an increased flow rate, through the probe 100. In one exemplary illustration, a cutting tool 104 has an inside diameter $D_1$ of 0.0116 inches, e.g., as measured along the blade portion 109, while the tubular body 102 inside diameter is 0.0156 inches. By removing the top half of the cutting tool 104 along the body portion 105, the effective diameter $D_2$ along the body portion 105 is increased to approximately 0.0136 inches. By assuming that the resulting geometry can be approximated as circular, this results in 47% less resistance along the body portion 105 of the cutting tool 104. If this reduced resistance is provided over half of the length of the cutting tool 104, flow may be increased by more than 30%, as approximated using Poiseuille's equation.

While a relatively large portion of the cutting tool 104 may be removed to enhance flow through the probe 100, other factors may limit how great a portion may be removed. For example, the increased flow offered by removal of a portion of the cutting tool 104 may be balanced against a minimum strength required of the cutting tool 104 to prevent buckling or other deformation during the use of the surgical probe 100. In other words, if too large a portion of the cutting tool 104 is removed, the cutting tool 104 may buckle as a result of its reduced and less structurally stable cross sectional area. At the same time, the cutting tool 104 is generally constrained within the tubular body 102, thereby providing some support.

Additionally, clogging of the fluid flow F may result if the modified/enlarged cross-sectional area is not maintained at least at the enlarged size up to the end of the tubular body 102. In other words, clogging problems may tend to be mitigated where cross-sectional area of the probe 100 is maintained or increased moving along the length of the probe 100 away from the cutting aperture 106. Accordingly, as shown in FIG. 1, the enlarged cross-sectional area of the fluid flow F may advantageously be maintained up to the second end 110 of the tubular body 102. Additionally, the tubular body 102 may be flared or enlarged at the second end 110, e.g., where the tubular body is attached to a base (not shown) of the surgical probe 100. For example, a flared portion 150 may be provided at the second end 110.

In another exemplary illustration, the cutting tool 104 may include a transitional portion 111 disposed between the body portion 105 and the blade portion 109. The transitional portion 111 may generally provide a transition between the relatively smaller cross-sectional flow area of the blade portion 109 and the relatively larger cross-sectional flow area of the body portion 105, thereby preventing a sudden change in cross-sectional flow area that might otherwise cause flow disturbances through the probe 100. For example, the transitional portion 111 may define an angled surface 113 extending between the body portion 105 and blade portion 109. Additionally, the angled surface 113 forms an angle α with an axis A-A of the tubular body 102 and/or cutting tool 104. As shown in FIG. 1, angle α may be less than 90 degrees. While any angle α may be employed that is convenient, an angle α that is less than 90 degrees may generally reduce weight of the cutting tool 104 while minimizing loss of overall strength of the cutting tool 104.

While the body portion 105 of the cutting tool 104 is illustrated as a generally semi-circular shape, i.e., with an upper half of a tubular section removed along portion $L_P$ of the cutting tool 104, any configuration providing only a partial extent about the inner circumference of the tubular body 102 may be employed. In one exemplary illustration, the body portion 105 may be replaced entirely by a solid rod (not shown) that supports the blade portion 109, extending from the blade portion 109 toward the fluid aperture 107 and being secured to a motor or other device that translates the blade portion 109 using the rod. Accordingly, any configuration of the cutting tool 104 may be employed that results in reduced flow resistance compared with a tubular section extending around the entirety of the inner periphery of the tubular body 102.

Referring now to FIG. 3, another exemplary surgical probe 100' is illustrated. The surgical probe 100', and in particular the cutting tool 104', includes multiple materials that further optimize the cutting tool 104' for increased flow. More specifically, the blade 112 may be formed of a first material that is optimized for greater strength and/or hardness to provide increased cutting effectiveness at the cutting aperture 106. By contrast, the remaining portion of the cutting tool 104 may be formed of a second material that is different from a material forming the blade 112. The second material may be optimized for other factors relevant to the body of the cutting tool 104', e.g., for the transmission of force from a motor of the surgical probe 100 to the blade 112. For example, the second material may have a high stiffness. In one illustration, the second material is a ceramic material having a high stiffness to enhance the transmission of force from the motor to the cutter. In another exemplary illustration, the first material is a stainless steel material.

The cutting tool 104' may also define two regions where the cutting tool 104' extends only partially about the inner circumference C of the tubular body 102. For example, the cutting tool 104' may include a body portion 105 that extends only partially about the inner circumference C of the tubular body 102, and a blade portion 109' that also extends only partially about the inner circumference C of the tubular body 102. The blade portion 109' and body portion 105 may be longitudinally spaced apart by an intermediate portion G. The blade portion 109' of the cutting tool 104' may define a length $L_1$ along the cutting tool 104' that includes the opening 114 in the cutting end of the cutting tool 104. The body portion 105 defines a length $L_2$ that also does not extend about the entirety of the inner circumference C of the tubular body 102. The lengths $L_1$ and $L_2$ are spaced apart longitudinally by the intermediate portion G. The intermediate portion G generally corresponds to a region of the cutting tool 104 that is fully formed about the circumference C of the tubular body 102, thereby increasing overall strength and/or stability of the cutting tool 104'.

As with cutting tool 104, the cutting tool 104' may include a transitional portion 111 disposed between the body portion 105 and the blade portion 109' that provides a transition between the cross-sectional flow area of the blade portion 109' and the relatively larger cross-sectional flow area of the body portion 105. Further, the transitional portion 111 may define an angled surface 113 extending between the body portion 105 and blade portion 109' that forms an angle α with an axis B-B of the tubular body 102 and/or cutting tool 104. The angle α may be any angle that is convenient, e.g., less than 90 degrees.

In addition to a top half of the cutting tool 104 being removed adjacent the second end of the tubular body 102, the cutting tool 104' also has an opening 114 along the blade portion 109'. For example, a portion of the cutting tool 104 is removed from a bottom side of the cutting tool 104 opposite the blade 112. Accordingly, opening 114 may be generally positioned opposite the blade 112 with the respect to the circumference of the cutting end of the cutting tool 104. The opening 114 may further increase flow along the cutting tool 104' and decrease overall weight of the cutting tool 104'.

In addition to gains in flow through the cutting tool 104, the removal of a portion of the cutting tool 104 along at least a portion of the length of the cutting tool 104 may generally prevent gas, e.g., air, from escaping from the probe 100 by way of the cutting aperture 106. More specifically, air or other gases may occasionally escape from the apparatus to which the tubular body 102 attaches, forming bubbles between the tubular body 102 and cutting tool 104 that can escape into an operating site through the cutting aperture 106. By allowing communication between the inside and outside of the cutting tool 104 downstream from the cutting aperature 106, e.g., by removing an upper half of the cutting tools 104, 104' as described above, any bubbles that leak into the probe 100 between the tubular body 102 and cutting tool 104 will tend to be entrained in the flow F, thereby carrying the bubbles away from the aperture 106 into the probe 100, thereby reducing the risk or gases escaping into an operating site, e.g., an ocular cavity.

Figure 4:
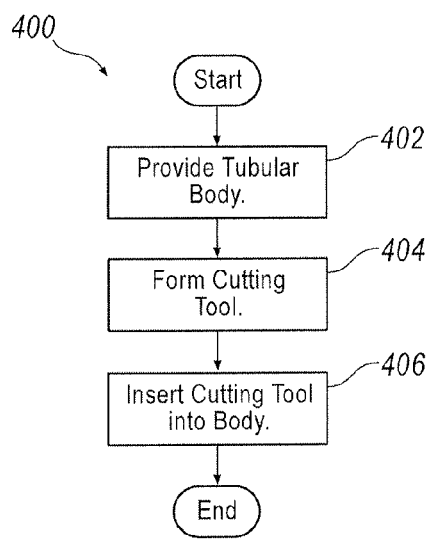
FIG. 4 illustrates a process flow diagram of an exemplary method of making a surgical probe.

Turning now to FIG. 4, an exemplary process 400 for assembling a surgical probe is illustrated. Process 400 may generally begin at block 402, where a tubular body is provided. For example, as described above, tubular body 102 may be provided that defines a cutting aperture 106 adjacent a first end 108 of the body 102. The tubular body 102 may further define a fluid passage F extending through the body 102 from the cutting aperture 106 to a second end 110 of the body 102. Process 400 may then proceed to block 404.

At block 404, a cutting tool may be formed. For example, as described above, a cutting tool 104, 104' may be formed having a body portion 105 and a blade portion 109, 109', respectively. A section of the generally tubular shape may be removed from one or more portions of the cutting tool 104, 104'. Accordingly, one or more portions of the cutting tool 104 may have a cross-sectional flow area that does not extend about an entirety of the inner circumference C of the tubular body 102, e.g., along body portion 105 and/or blade portion 109.

The cutting tool 104, 104' may be formed using any process that is convenient. In one exemplary illustration, a tubular blank or stock may be provided that substantially defines a tubular shape having a circular cross-section. A portion of the tubular blank may be removed, e.g., such that the body portion 105 of the cutting tool 104 extends only partially about an inner circumference C of the tubular body 102. In another exemplary illustration, a portion of the tubular blank may be removed along a blade portion 109' such that the blade portion 109' extends only partially about a circumference of the tubular body 102. For example, in one illustration, portions of the tubular blank may be removed by either cutting or grinding the tubular blank, or by applying an electrical discharge machining process to the tubular blank, thereby removing material from the cutting tool 104, 104'. As noted above, both the tubular body 102 and the cutting tool 104, may define generally cylindrical inner surfaces. Any other shapes may be employed that are convenient.

Proceeding to block 406, the cutting tool may be inserted into a fluid passage of the tubular body 102. For example, cutting tool 104 may be inserted into tubular body 102 such that a blade 112 of the cutting tool 104 is positioned adjacent the cutting aperture 106. The cutting tool 104 may be configured to allow fluid flow through the cutting tool 104.

Additionally, as also described above, after insertion of the cutting tool 104 into the tubular body 102, the cutting tool 104 and tubular body 102 may generally cooperate to define a cross sectional area $A_2$ normal to the fluid flow F. The cross sectional area $A_2$ may be larger than a cross sectional area $A_1$ defined by an inner tubular surface of the cutting tool 104.

Accordingly, surgical probe 100 allows for increased fluid flow through the surgical probe 100 as compared with probes utilizing a full tubular shaped cutting tool. In some illustrations, multiple portions of a cutting tool 104 may be removed, e.g., from a tubular stock, further increasing flow through the probe 100.

Reference in the specification to "one example," "an example," "one embodiment," or "an embodiment" means that a particular feature, structure, or characteristic described in connection with the example is included in at least one example. The phrase "in one example" in various places in the specification does not necessarily refer to the same example each time it appears.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A vitrectomy probe, comprising:
    a tubular body defining a cutting aperture adjacent a first end of the body and a fluid passage through the body from the cutting aperture to a second end of the body; and
    a cutting tool disposed within the fluid passage, the cutting tool configured to allow fluid flow through the cutting tool and to reciprocate within the tubular body to move across the cutting aperture thereby cutting ophthalmic tissue that enters the cutting aperture, the cutting tool including:
        a body portion;
        a blade portion disposed at a first end of the body portion, the blade portion having a blade configured to cut material at the cutting aperture; and
        a transitional portion disposed between the blade portion and the body portion, the transitional portion defining an angled surface extending between the blade and body portions, the angled surface defining an angle less than 90 degrees with a longitudinal axis of the cutting tool;
    wherein the body portion extends only partially about an inner circumference of the tubular body; and
    wherein the blade portion extends only partially about a cutting end of the cutting tool adjacent the cutting aperture, the cutting tool defining an opening in the cutting end, the opening positioned opposite the blade with respect to the circumference of the cutting end and defining a second angled surface, the second angled surface defining an angle less than 90 degrees with the longitudinal axis of the cutting tool.

2. The surgical probe of claim 1, wherein the cutting tool defines a shape corresponding to an inner surface of the tubular body along the blade portion of the cutting tool.

3. The surgical probe of claim 1, wherein the cutting tool extends about no more than one half of the inner circumference of the tubular body along the body portion of the cutting tool.

4. The surgical probe of claim 1, wherein the body portion of the cutting tool cooperates with the tubular body to define a first cross-sectional area normal to a fluid flow through the tubular body, the first cross-sectional area being larger than a second cross-sectional area normal to the fluid flow defined by the cutting tool.

5. The surgical probe of claim 1, wherein the body portion of the cutting tool defines a generally semi-circular shape.

6. The surgical probe of claim 1, wherein the first end of the tubular body is configured to be inserted into a surgical incision, and the second end is configured to be secured to a surgical tool for fluid exchange therewith, the second end defining a fluid aperture in fluid communication with the cutting aperture.

7. The surgical probe of claim 1, wherein the blade portion of the cutting tool is formed of a first material, and the body portion of the cutting tool is formed of a second material different from the first material.

8. The surgical probe of claim 1, wherein the body portion of the length of the cutting tool is at least one half of the length.

* * * * *